(12) United States Patent
Menard et al.

(10) Patent No.: US 6,927,239 B1
(45) Date of Patent: Aug. 9, 2005

(54) METHODS AND COMPOSITIONS FOR THE ATTENUATION AND/OR PREVENTION OF STRESS/CATABOLIC RESPONSES

(75) Inventors: Michael Menard, Gurnee, IL (US); Susie Rockway, Grayslake, IL (US)

(73) Assignee: Pharmanutrients, Lake Bluff, IL (US)

( * ) Notice: Subject to any disclaimer, the term of this patent is extended or adjusted under 35 U.S.C. 154(b) by 0 days.

(21) Appl. No.: 10/333,299

(22) PCT Filed: Aug. 2, 2000

(86) PCT No.: PCT/US00/21047

§ 371 (c)(1),
(2), (4) Date: Jul. 3, 2003

(87) PCT Pub. No.: WO02/09692

PCT Pub. Date: Feb. 7, 2002

(51) Int. Cl.[7] ............................................... A61K 31/20
(52) U.S. Cl. ..................................................... 514/560
(58) Field of Search ....................................... 514/560

(56) References Cited

U.S. PATENT DOCUMENTS

| | | | |
|---|---|---|---|
| 4,981,844 A | | 1/1991 | Alexander et al. |
| 5,430,066 A | * | 7/1995 | Cook et al. .................. 514/558 |
| 5,603,959 A | | 2/1997 | Horrobin et al. |
| 5,886,037 A | | 3/1999 | Klor et al. |
| 6,034,132 A | * | 3/2000 | Remmereit .................. 514/560 |
| 6,060,514 A | * | 5/2000 | Jerome et al. .............. 514/560 |

FOREIGN PATENT DOCUMENTS

| | | | |
|---|---|---|---|
| WO | WO 96/34855 | * | 11/1996 |
| WO | WO 98/18751 | * | 5/1998 |
| WO | WO 99/29317 | | 6/1999 |

OTHER PUBLICATIONS

Cook et al., Advances in Conjugated Linoleic Acid Research (1999), vol. 1, 226-237 AOCS Press, Champaign, Ill.*
U.S. Appl. No. 10/333,299, filed Jan. 17, 2003, Menard et al.
U.S. Appl. No. 10/333,297, filed Jan. 17, 2003, Menard et al.
U.S. Appl. No. 10/333,298, filed Jan. 17, 2003, Menard et al.
U.S. Appl. No. 10/333,295, filed Jan. 17, 2003, Menard et al.

* cited by examiner

*Primary Examiner*—Raymond J. Henley, III
(74) *Attorney, Agent, or Firm*—Bell, Boyd & Lloyd LLC

(57) ABSTRACT

Methods and compositions for treating metabolic stress are provided. The method comprises the steps of administering a therapeutically effective amount of conjugated linoleic acid.

2 Claims, No Drawings

METHODS AND COMPOSITIONS FOR THE ATTENUATION AND/OR PREVENTION OF STRESS/CATABOLIC RESPONSES

This application claims priority to the international application PCT/US00/21047 filed Aug. 2, 2000 pursuant to 35 U.S.C. 371.

BACKGROUND OF THE INVENTION

The present invention relates generally to compositions and methods for the treatment of disease states. More specifically, the present invention relates to compositions and methods for managing or preventing catabolic stress.

Many diseases are known to be associated with metabolic stress condition. These acute or chronic illnesses can either initiate and/or maintain a metabolic stress condition. The metabolic stress condition has been demonstrated clinically through such events as adverse response to trauma, obesity, cancer, transfusions, acute and chronic diseases, various types of surgery, immunological disorders, and infections.

Although such metabolic stress is known and has been demonstrated, there are few therapeutic options for treating such conditions. As a result, over a period of time, individuals remain in a persistent catabolic state, unable to overcome the physiological effects of these catabolic agents.

An example of such a condition is that associated with chronic obesity. In this condition, despite adherence to a variety dietary and medical interventions, these individuals are unable to lose weight due, in part, to the underlying metabolic stress response. Such a response may be characterized by chronically elevated levels of cortisol, glucagon, adrenocorticotropic hormones, cytokines and other associated compounds.

Metabolic stress can also be associated with cachexia. In this regard, due to illness, such as cancer or chronic immune disorders, metabolic stress can be induced that results in cachexia.

Another example of a metabolic stress condition relates to the delayed stress response sometimes accompanying cardiac bypass surgery. While most patients exhibit favorable results for up to 60 days following such a procedure, evidence suggests the existence of a delayed stress response which may significantly influence morbidity and mortality following cardiac bypass surgery. This delayed response can occur for up to two years after the surgery.

To address stress response accompanying acute and chronic illness as well as to treat stress response associated with invasive procedures and trauma, generally steroidal compounds have been administered. It is believed that although there is a moderate symptomatic suppression of the stress response through the use of steroids, this treatment can be accompanied by significant side effects and long-term consequences.

Accordingly, there is a need for improved methods of treatment and compositions for treating and preventing metabolic stress.

SUMMARY OF THE INVENTION

The present invention relates to methods and compositions for the attenuation, prevention, and/or management of the metabolic stress/catabolic response. In this regard, the present invention can be used to address metabolic stress conditions such as those associated with but not limited to, for example, various types of surgery, auto-immune disorders, and infections.

To this end, the present invention provides a method for preventing or minimizing the onset of metabolic stress in an individual that may be susceptible to same, comprising the step of administering a therapeutically effective amount of a composition including conjugated linoleic acid.

In an embodiment, approximately 500 mg to about 10,000 mg per day of conjugated linoleic acid are administered.

In an embodiment, the individual recently had surgery.

In an embodiment, the individual recently had an acute illness.

In an embodiment, the individual has a chronic illness.

In an embodiment, the conjugated linoleic acid is either a pure isomer of octadecadienoic acid, or a mixture of octadecadienoic acid isomers selected from the group consisting of: cis-8, cis-10; cis-8, trans-10; trans-8, cis-10; trans-8, trans- 10; cis-9, cis-11; cis-9, trans-11; trans-9, cis-11; trans-9, trans-11; cis-10, cis 12; cis-9, trans-12; trans-9, cis-12; trans-10, trans-12; cis-11, cis-13; cis-11, trans-13; trans-11, cis-13; trans-11, trans-13 octadecadienoic acid; metabolites thereof, including but not limited to 18:3 cis-6, cis-9, trans 11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; as well as precursors or derivatives thereof.

In an embodiment, the composition includes a flavor.

In an embodiment, the composition includes an artificial sweetener.

In another embodiment of the present invention, a method of reducing the effects of metabolic stress in an individual suffering from metabolic stress is provided. The method comprising the step of administering a therapeutically effective amount of a composition including conjugated linoleic acid.

In an embodiment, approximately 500 mg to about 10,000 mg per day of conjugated linoleic acid are administered.

In an embodiment, the individual is preparing for, or recovering from invasive surgery.

In an embodiment, the individual has a chronic illness.

Still further, the present invention provides a method of treating chronic obesity. The method comprising the step of administering a therapeutically effective amount of a composition including conjugated linoleic acid to an individual suffering from chronic obesity.

Additionally, the present invention provides a method of preventing or treating cachexia associated with metabolic stress, comprising the step of administering a therapeutically effective amount of a composition including conjugated linoleic acid to a patient who is expected to experience cachexia, or is having cachexia associated with metabolic stress.

Additionally, the present invention provides a method of reducing the risk of morbidity and mortality of a patient who has had cardiac bypass surgery comprising the step of administering a therapeutically effective amount of a composition including conjugated linoleic acid to a patient that will undergo or has had cardiac surgery.

In an embodiment, the composition is administered to the patient some time prior to or after the surgery but prior to two years after the surgery.

An advantage of the present invention is that is provides a method and composition for the attenuation of metabolic stress and/or catabolic response.

A further advantage of the present invention is that it provides a method for preventing or at least reducing the risk of metabolic stress.

An additional advantage of the present invention is that it provides a method and composition for treating persistent catabolic state.

Another advantage of the present invention is that it provides a method and composition for treating chronic obesity related to metabolic stress.

Still, an advantage of the present invention is that it provides a method and composition for assisting patients who are unable to prevent weight gain or to lose weight.

Furthermore, an advantage of the present invention is that it provides a method and composition for reducing morbidity and mortality following cardiac bypass surgery.

Still further, an advantage of the present invention is that it provides a method and composition for aiding in the recovery of patients who have had invasive surgery.

Additionally, an advantage of the present invention is that it provides a method of preventing or treating metabolic stress and/or cachexia associated with illness.

Still further, an advantage of the present invention is that is provides a method and composition for enhancing the general health and well-being of patients suffering from metabolic disfunctions.

These and other advantages and features present invention are described in and will be apparent from the detailed description of pressing preferred embodiment.

DETAILED DESCRIPTION OF PRESENTLY PREFERRED EMBODIMENTS

The present invention provides methods and compositions for the attenuation and prevention of metabolic stress and/or catabolic response. The compositions of the present invention can be administered as a nutritional supplement, over-the-counter product, or pharmaceutical product, or as a component of pharmaceutical agents.

Pursuant to the present invention the composition includes conjugated linoleic acid. Conjugated linoleic acid is utilized to influence those physiological processes associated with induction and maintenance of catabolic stress. Through its modulating effect on specific cytokines and pro-inflammatory prostaglandins, conjugated linoleic acid minimizes the expression of IL-1, IL-6, TNF$\alpha$, and PGE$_2$.

Generally, pursuant to the present invention, it is envisioned that the composition of the present invention will be administered for a defined period before and/or after a period of stress initiation. The conjugated linoleic acid will serve to minimize the stimulation and/or propagation of the stress response. This will enhance the general health and well-being as well as improve recovering from conditions initiating metabolic stress. Such conditions include, but are not limited to, cardiac surgery, acute and chronic illnesses, asthma, and other metabolic dysfunctions.

The compositions of present invention may minimize the stress response. The compositions will also assist in the restoration of the normal homeostatic mechanisms underlying metabolic processes.

The ingredients that are used in the compositions of present invention are preferably all naturally occurring substances or derived therefrom; the active ingredients are all naturally occurring substances or derived therefrom. As compared to prior treatments and compositions, the present invention provides a less expensive alternative with no foreseeable side effects.

Pursuant to the present invention, the method and composition comprises administering conjugated linoleic acid. If desired, the composition can include non-active ingredients and/or agents such as flavors, artificial sweeteners, excipients, etc. The product of the present invention is intended to provide a physiologically based means to aid in maintaining normal physiological homeostasis.

Conjugated linoleic acid refers to a group of dienoic derivatives of linoleic acid that occur naturally in milk and meat of ruminating animals. It can be synthesized in the laboratory and is available commercially as a dietary supplement.

Conjugated linoleic acid is believed to be absorbed efficiently into the body in a manner similar to that of other fatty acids, e.g., linoleic acid. The safety of conjugated linoleic acid has been demonstrated in detailed toxicological assessments and through extensive use in humans, both as a naturally occurring substance and as a dietary supplement. It is believed that conjugated linoleic acid is safe for human consumption.

Pursuant to the present invention, the conjugated linoleic acid can be conjugated linoleic acid such as that set forth in U.S. Pat. No. 5,986,116 the disclosure of which is incorporated herein by reference.

In an embodiment, the conjugated linoleic acid is either a pure isomer of octadecadienoic acid, or a mixture of octadecadienoic acid isomers selected from the group consisting of: cis-8, cis-10; cis-8, trans-10; trans-8, cis-10; trans-8, trans-10; cis-9, cis-11; cis-9,trans-11; trans-9, cis-11; trans-9, trans-11; cis-10, cis-12; cis-9, trans-12; trans-9, cis-12; trans-10, trans-12; cis-11, cis-13; cis-11, trans-13; trans-11, cis-13; trans-11, trans-13 octadecadienoic acid; metabolites thereof, including but not limited to 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; as well as precursors or derivatives thereof.

In an embodiment, the present invention comprises a method comprising providing to a patient approximately:

500 mg to about 10,000 mg of conjugated linoleic acid per day.

In a most preferred embodiment of the method, the method provides approximately:

500 mg to about 6,000 mg of conjugated linoleic acid per day.

Pursuant to the present invention, the composition can be taken as a dietary supplement or a pharmacological product.

By way of example and not limitation, contemplative examples of the present invention are as follows:

EXAMPLE NO. 1

In order to treat stress-catabolic response sufficient product will be administered so that the patient receives 500 mg to 10,000 mg of conjugated linoleic acid per day. It is believed that this level of conjugated linoleic acid will at least reduce the effects of metabolic stress.

EXAMPLE NO. 2

In order to treat cachexia associated with chronic illness, sufficient product would be administered to provide 500 mg to about 10,000 mg of conjugated linoleic acid per day. It is believed that at such levels the cachexia should be at least reduced.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A method of reducing the risk of morbidity for a patient who will have or has had cardiac bypass surgery comprising the step of administering a therapeutically effective amount of a composition including conjugated linoleic acid to said patient.

2. The method of claim 1 wherein the composition is administered at any time prior to two years after the bypass surgery.

* * * * *